US008570508B2

(12) United States Patent
Rose et al.

(10) Patent No.: US 8,570,508 B2

(45) Date of Patent: Oct. 29, 2013

(54) PRESSURE-PROOF PROBE

(75) Inventors: Andreas Rose, Langenfeld (DE); Martin Gotter, Köln (DE); Thomas Schwindack, League City, TX (US); Christoph Schwinning, Leverkusen (DE); Patrick Eckert, Kandern (DE); Holm Kändler, Auggen (DE); Christof-Krzysztof Koltunski, Merzhausen (DE); Hannes Ebding, Haltingen (DE)

(73) Assignee: Bayer MaterialScience AG, Leverkusen (DE)

( * ) Notice: Subject to any disclaimer, the term of this patent is extended or adjusted under 35 U.S.C. 154(b) by 208 days.

(21) Appl. No.: 12/817,559

(22) Filed: Jun. 17, 2010

(65) Prior Publication Data

US 2010/0321690 A1 Dec. 23, 2010

(51) Int. Cl.

*G01J 3/28* (2006.01)

*G01N 21/00* (2006.01)

(52) U.S. Cl.

USPC .......... 356/326; 356/436

(58) Field of Classification Search

USPC .......... 356/300–334, 244, 246, 436, 442

See application file for complete search history.

(56) References Cited

U.S. PATENT DOCUMENTS

| | | | | |
|---|---|---|---|---|
| 4,835,389 | A | 5/1989 | Doyle | |
| 4,988,195 | A | 1/1991 | Doyle | |
| 5,046,854 | A * | 9/1991 | Weller et al. | 356/440 |
| 5,051,551 | A | 9/1991 | Doyle | |
| 5,120,129 | A * | 6/1992 | Farquharson et al. | 356/246 |
| 5,170,056 | A | 12/1992 | Berard et al. | |
| 5,185,834 | A | 2/1993 | Day et al. | |
| 5,223,716 | A * | 6/1993 | Rossiter | 250/343 |
| 5,418,615 | A * | 5/1995 | Doyle | 356/436 |
| 6,484,562 | B2 * | 11/2002 | Fabinski et al. | 73/31.05 |
| 6,512,156 | B1 * | 1/2003 | Timmermans et al. | 585/501 |
| 2002/0129638 | A1 | 9/2002 | Fabinski et al. | |
| 2005/0040335 | A1 | 2/2005 | Hauschild et al. | |
| 2006/0047170 | A1 | 3/2006 | Keggenhoff et al. | |

FOREIGN PATENT DOCUMENTS

| | | | |
|---|---|---|---|
| DE | 4038354 | A1 | 6/1992 |
| DE | 4414975 | A1 | 11/1995 |
| DE | 4414975 | A1 * | 11/1995 |
| DE | 10230857 | A1 | 2/2004 |
| DE | 102004041777 | A1 | 3/2006 |
| EP | 1134582 | A2 | 9/2001 |
| EP | 1512960 | A1 | 3/2005 |
| EP | 2108937 | A1 | 10/2009 |
| GB | 2255194 | A | 10/1992 |

* cited by examiner

*Primary Examiner* — Gregory J Toatley

*Assistant Examiner* — Dominic J Bologna

(74) *Attorney, Agent, or Firm* — Novak Druce Connolly Bove + Quigg LLP

(57) ABSTRACT

A probe for monitoring a pressurised process space includes a casing enclosing a cavity and having a first window configured to be brought into contact with the process space, and a second window. A sealing means is configured to seal the first window to the casing. At least once coupling line is disposed within the cavity between the first and second windows and is configured to guide electromagnetic radiation entering through one of the two windows to the other of the two windows. A method for monitoring a pressurised process space, in which one or more hazardous substances occur, is also disclosed.

16 Claims, 2 Drawing Sheets

80 80 61 2 10 10 40 50 40 30 50 50 30 85 62 20 17 15

40
50
15
17
50
2
20
61
40
62
50
10
30
80
85
80
10
30

40
40
50
50
15
60
50
50
40
2
50
30
20
40
10
30
50
55
55

PRESSURE-PROOF PROBE

PRIORITY

Priority is claimed under 35 U.S.C. §119 to German patent application No. 10200905677.6, filed Jun. 17, 2009. The disclosure of this priority application is incorporated herein in its entirety.

BACKGROUND OF THE INVENTION

1. Field of the Invention

The field of the present invention relates to a probe for monitoring a pressurised process, and to a method for monitoring a process in which one or more hazardous substances occur.

2. Background

Chemical production processes can be controlled efficiently when the instantaneous composition and quality of starting substances, reaction mixtures or products in the various stages of the production process are known. Online spectroscopic measurement methods allow direct continuous monitoring of a running process. Optical probes are of particular importance here, since analysis by means of optical probes takes place noninvasively in direct sample contact and works without elaborate sampling or preparation of the substance mixture to be analysed.

For usability of optical probes, access to the substance or substance mixture to be examined is crucial. Chemical processes are conventionally carried out in closed reactor containers and/or pipelines. These are generally opaque for the wavelength range which is used for the analysis.

It is therefore necessary to provide windows which are transparent for the wavelength range being used, in order to make it possible to track the processes in the reactor space or the connected pipelines.

Owing to possible toxic properties of the substances to be analysed in the process, stringent requirements are placed on these windows in respect of leaktightness, particularly for processes which are operated under high pressure.

For the input and output of electromagnetic radiation in a reactor, so-called coupling lines are often used. These are flexible lines which make it possible to transmit electromagnetic radiation over a certain path without accurate positioning of the optical components along this path being necessary. Above all, glass fibre cables from the telecommunications field are known. In process monitoring or online analysis, so-called waveguide couplings or special silver halide or fluoride glass light guides are used for applications in the medium infrared range. In the near infrared range and ultraviolet/visible range (UV/Vis: 200-700 nm), it is preferable to use quartz light guides which are available with low attenuation in this spectral range.

The publication DE10230857A1 describes a process window for online analysis with pressure monitoring. At two opposite positions of a pipe, two windows are formed through which electromagnetic radiation can be input into the pipe and output again. Each window is placed into a threaded insert. Respectively, 2 seals between the threaded insert and the pipe, and between the window and the threaded insert, ensure sealing of the pipe interior from the outside world. The threaded insert is screwed into a holder (measurement cell body), which is connected to the pipe. Both between the threaded insert and the window, and between the threaded insert and the holder, there are cavities between the first and second seals, and these are connected to one another via bores. The cavities are sealed off from the outside world by means of a seal between the threaded insert and the holder. There is double sealing of the pipe interior from the outside world by means of the process window. Besides this double security, the device makes it possible to monitor leaks. If one of the seals, which is in contact with the pipe interior, loses its effect, substances emerge from the pressurised pipe into the cavities. The rising pressure can be registered by means of a pressure sensor, which is connected to the cavities.

The dimensions and geometries of optical probes, and the optical components contained in them, do not allow double sealing respectively at a window in the form of the process window disclosed in DE10230857A1. It is furthermore generally known that light guides and waveguides are mechanically loadable much less strongly than, for example, a quartz glass or sapphire window, as are used in a process window according to DE10230857A1.

Accordingly, pressure-tight sealing of a light guide or waveguide is also more demanding and/or more elaborate.

In the probes commercially available nowadays, the light guide or waveguide per se is therefore not sealed off from the process space, but instead the light is input from a source via a first coupling line through a window into the process space and output again through another window or the same window, in order to reach a detector via a second coupling line, the sealing of the process space from the outside world (in which the coupling lines are located) being carried out by means of a seal between the window and the process space.

This is disclosed, for example, in patent specification DE4414975C2. In FIG. 2 of the said patent specification, a pressure-proof window is sealed off from a casing by a seal. In the casing, light guides are arranged which input and output the light through the window into the reaction space. As a particular feature in the device in FIG. 2, the light guides are additionally connected to the casing by means of an adhesive. These adhesive bonds are intended to form pressure-proof barriers. Such an additional pressure barrier, however, is not generally usable since many substances, for example solvents or strong oxidising agents, dissolve the adhesive or react with the adhesive so that this barrier is destroyed. An adhesive bond is furthermore not a defined connection which ensures process-compatible sealing in respect of pressure-tightness, thermal stability and chemical stability.

Other probes described in the prior art comprise a simple seal, by which the process space is sealed off by means of a window from the probe optics (see for example U.S. Pat. Nos. 5,185,834, 5,170,056, 4,835,389, 4,988,195, 5,051,551, DE-A4038354). In processes which take place under pressure, there is a risk of a window breaking or a leak at a seal, so that substances from the process can reach the outside world. Besides the risk of damaging the probe optics, in the case of toxic substances in particular there is also a risk of harming humans and the environment.

On this basis, a probe is desired which allows online monitoring of a pressurised process and has safety precautions which effectively prevent substances from emerging from the process space into the environment if a seal placed in contact with the process space fails.

SUMMARY OF THE INVENTION

The present invention is directed toward a probe and a method for monitoring a process space in which one or more hazardous substances occur. The probe includes a casing enclosing a cavity and having first and second windows, with the first window being configured to be brought into contact with the process space. A sealing means is configured to seal the first window to the casing. At least one coupling line is disposed within the cavity, between the first and second windows, and configured to guide electromagnetic radiation entering through one of the two windows to the other of the two windows.

Several different options may be incorporated into the probe, either individually or in combination. For example, the first window may be configured to be replaceable, and/or the second window may be configured to be integrated pressure-tightly into the casing. As another option the casing may include connections for flushing the cavity. As yet another option, the probe may include a pressure sensor for monitoring the pressure within the cavity.

The method includes inputting electromagnetic radiation into a first cavity within a casing through a first pressure-tight window and into a first coupling line disposed within the first cavity. Using the first coupling line, the electromagnetic radiation is transmitted out of the first cavity and into the process space through a second pressure-tight window. Depending upon the configuration used to implement the method, the electromagnetic radiation may be received back into the first cavity, or into a second cavity through a third pressure-tight window lying opposite the second pressure tight window. When received back into the first cavity, the received electromagnetic radiation enters a second coupling line and is transmitted through the first pressure-tight window and to a spectrometer. When received into a second cavity, the received electromagnetic radiation enters a second coupling line disposed in the second cavity and is transmitted through a fourth pressure-tight window and to a spectrometer.

Accordingly, an improved pressure probe and method of monitoring a process space are disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
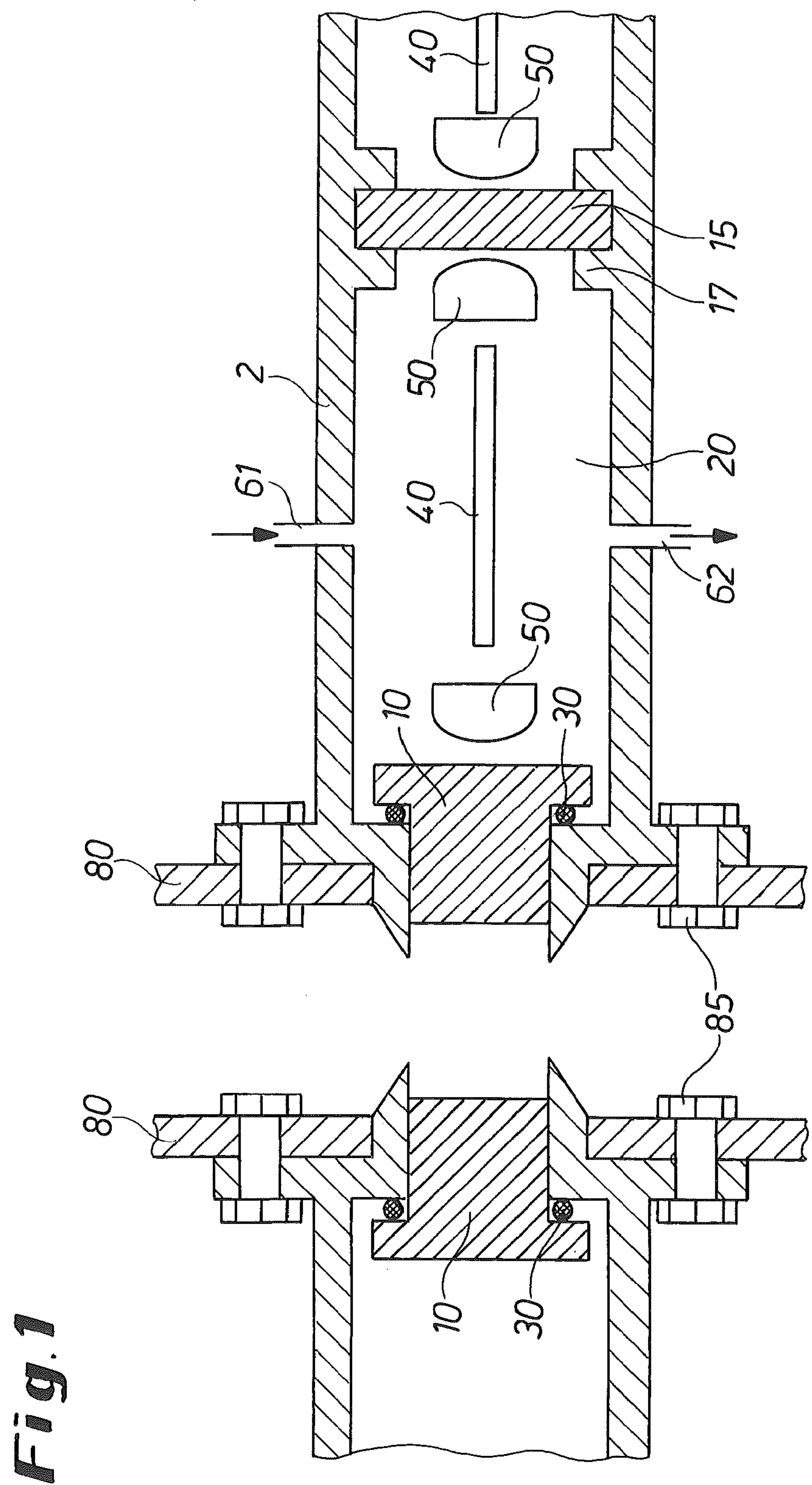
FIG. 1 shows a schematic representation of a probe for monitoring a process in a pipe.

In a preferred embodiment, the probe is configured as a process window. In order to monitor a process in a reactor or pipe, two of the process windows are arranged at opposite positions of the reactor or pipe so that there is a gap with a defined width between the windows. Electromagnetic radiation can be input into the process space through one process window. For spectroscopic analysis, absorption of the electromagnetic radiation takes place inside the layer between the two opposite process windows. The transmitted radiation is output from the process space through the second process window. FIG. 1 shows such an arrangement of two process windows in a schematic representation in cross section. They are flanged onto a pipeline (80) by means of screw connections (85). The right-hand process window shows all of the essential components of a probe. A casing (2) is used to receive a first window (10), which is in contact with the process space. A second window (15) is furthermore connected to the casing. The casing and the windows form a cavity (20). The latter is sealed off from the process space by sealing means (30).

The second window is firmly placed in a window frame, for example by means of a soldered connection, whereas the first window is connected releasably to the casing and can be replaced.

Connections (61, 62) are fitted in the casing, which make it possible to flush the cavity (indicated by the arrows). A light guide (40) as a coupling line provides an optical connection between the first and second windows. There is preferably also a light guide, which leads to the source of electromagnetic radiation or the detector, on the opposite side of the second window (15) from the cavity (20).

It is known to the person skilled in the art that the transmission of electromagnetic radiation from one light guide through a window to another light guide is not readily possible, since the light guides have only a small cross section and direct coupling of the light guides requires very accurate positioning of them across the window. Furthermore, electromagnetic radiation emerges from a light guide in the form of divergent radiation, so that only a small part of the radiation emerging from one light guide would actually enter the other light guide on the opposite side of the window.

The probe therefore has lenses (50) which guide a widened, collimated beam through the window and input it again into a light guide. The use of such collimation lenses therefore allows not only the input and output of electromagnetic radiation into and from a process space, but also the transmission of signals through a pressure-tight window.

Figure 2:
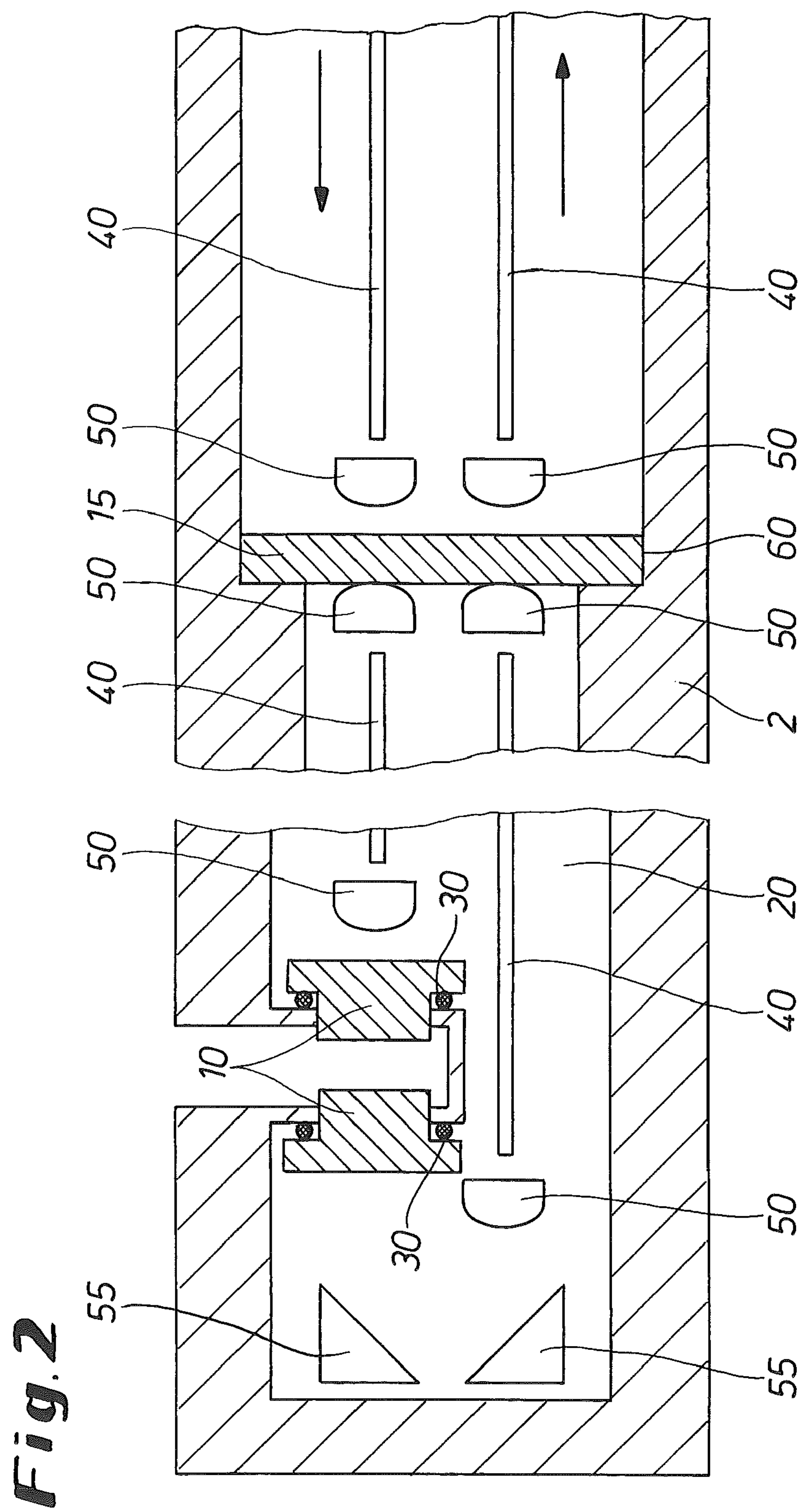
FIG. 2 shows a schematic representation of an immersible probe.

In another preferred embodiment, the probe is provided as an immersible probe. An example of such an immersible probe is represented schematically in FIG. 2. References which are the same in FIGS. 1 and 2 respectively have the same meaning. Two windows (10) are provided, which can be brought in contact with a process space. Between the windows (10), there is a gap with a defined width so that spectroscopic examinations on a defined layer thickness are possible.

Electromagnetic radiation is input through a first light guide (40) into the probe, and output from the probe through a further light guide (denoted by arrows).

A cavity (20) is provided, which can be sealed off from the process space by sealing means (30). A second window (15) is furthermore connected to the casing, and seals the cavity off from the outside world. This second window is fitted firmly in a window frame (60), for example by means of a soldered connection. The transmission of electromagnetic radiation through a window takes place with the aid of lenses (50). Mirrors (55) ensure deflection of electromagnetic radiation.

The casing is used to hold a first window and a second window. A casing is intended to mean a body into which windows can be introduced pressure-tightly. The casing may be configured in one piece or a plurality of pieces. If it is configured in a plurality of pieces, then the various components of the casing may be connected pressure-tightly to form a continuous body.

The casing is preferably configured as a hollow cylinder.

When using the probe for process monitoring, the first window is in contact with the process space. Here, a window is intended to mean a component of the probe which is at least partially transparent for electromagnetic radiation. The window is preferably at least partially transparent for electromagnetic radiation in the wavelength range of from 200 to 700 nm (UV/Vis) and/or in the wavelength range of infrared (IR) and/or near infrared (NIR). Partial transparency is intended to mean at least 50% transparency, i.e. at least 50% of the incident radiation passes through the window.

The casing has means which allow pressure-proof connection between the casing and the container (pipe, reactor)

which encloses the process space. Sealing means are furthermore provided, which seal off the window on the process side in the casing. Sealing means are intended to mean the means known to the person skilled in the art for the pressure-proof sealing of windows, for example O-ring seals.

The casing has at least one further window, which is referred to here as the second window. The casing, the first window and the second window enclose a cavity. Sealing means on the second window seal off the cavity from the outside world. At least one coupling line is arranged in the cavity, between the first and second windows, so that electromagnetic radiation can be guided through one window, via the coupling line and through the other window.

A coupling line is intended to mean a preferably flexible body, which can transmit radiation over a path. The coupling line preferably has a low attenuation. Preferred coupling lines are light guides for the transmission of electromagnetic radiation in the NIR or UV/Vis range, or waveguides or light guides for the transmission of electromagnetic radiation in the IR range.

The coupling line provides a connection for electromagnetic radiation between the windows. The arrangement of the windows, casing, sealing means and coupling line is configured so that the optical junction through the window also represents a double pressure barrier which prevents substances from the process from emerging into the outside world.

If the first window placed in contact with the process space breaks, or if its seal fails, substances from the process space can thus enter the cavity which is formed by the window and the casing. The further seal of the second window effectively prevents substances from the process space from passing through the cavity into the outside world. In a preferred embodiment, the sealing means of the first window are replaceable (for example O-ring seals), whereas the second window is preferably connected non-releasably to the casing (for example by means of a soldered connection). It is also conceivable to use replaceable seals for both windows.

The probe preferably has means which allow the cavity to be monitored. In a preferred embodiment, connections which make it possible to flush the cavity are provided on the casing. If a leak occurs, then a substance which enters the cavity will be extracted by means of the flushing gas and can be detected. In another preferred embodiment, a pressure sensor is provided which monitors the pressure in the cavity. Further possibilities for monitoring the cavity may be envisaged.

The probe is suitable for the optical monitoring of, in particular, pressurised processes. Monitoring is intended to mean the tracking of one or more process parameters as a function of time, which can provide information about the process. The monitoring involves recording one or more parameters and evaluating the measured parameter values. The evaluation may, for example, consist in comparing a measured parameter value with a setpoint value.

The preferably process-integrated checking of the quality features and process parameters serves for monitoring correct operation, early detection of irregular statuses and processes, and concomitant restriction of the impact of faults.

Process monitoring can therefore be used as a warning system in order to avoid expensive process interruptions and system down times. The setpoint-actual comparison in real time, which is possible with process-integrated monitoring, can also be used to deliberately influence processes by changing control variables (process regulation).

Optical monitoring is intended to mean that the interaction of a substance present in the process with electromagnetic radiation is used to record a process parameter. For example, the concentration of a substance in a process may be tracked by measuring the absorption of incident electromagnetic radiation (see for example EP 1512960B1).

The probe is suitable in particular for monitoring processes in which one or more hazardous substances occur. A hazardous substance is intended to mean a substance which may be harmful for humans, animals and/or the environment. Hazardous substances may for example be toxic, corrosive and/or carcinogenic. One example of a hazardous substance is phosgene.

The hazardous substance may for example be used as an educt in the process to be monitored, occur as an intermediate product or be formed as an end product. The probe makes it possible to monitor the process in which the hazardous substance occurs, so as to ensure that the process is taking place correctly. The double sealing of the window on the process side from the outside world will ensure that the hazardous substance does not reach the outside world if the window on the process side breaks or a seal on the window on the process side fails. If the window on the process side breaks, the hazardous substance can enter a cavity which may be constantly monitored, in order to detect a leak immediately.

The probe, including variations thereof, may be used for monitoring a process, in particular a pressurised process, in which one or more hazardous substances occur. In a preferred embodiment, the probe is used for monitoring a process in which phosgene occurs.

The method for monitoring a process in which one or more hazardous substances occur is characterised in that electromagnetic radiation is input through a pressure-tight window into a coupling line and, by means of the coupling line, is input into the process space through a further pressure-tight window on the process side.

The pressure-tight windows enclose a cavity, which is sealed off from the process space and the outside world. At least one coupling line between the windows optically connects them to one another, so that electromagnetic radiation can travel through one window, via the coupling line to the other window, and through this other window.

In a preferred embodiment of the method, the cavity is monitored in respect of substances passing from the process space into the cavity. This is done for example by means of pressure measurement, spectroscopically, by mass spectrometry or by gas chromatography.

In a preferred embodiment, the electromagnetic radiation, which has been input in the described manner into the process space, is output again from the process space through a further window on the process side, lying opposite the window on the process side, input into a coupling line and guided through a pressure-tight window to a spectrometer, in order to examine it for a modified intensity of at least one wavelength.

Preferably, after output from the process space, the electromagnetic radiation is guided to a spectrometer through at least one window which was used for input into the process space Preferably IR (400-4000 $cm^{-1}$), NIR (4000-14000 $cm^{-1}$) and/or UV/V is (200-700 nm) radiation is used as the electromagnetic radiation.

In a preferred embodiment of the method, a process in which phosgene occurs as a hazardous substance is monitored.

LISTING OF REFERENCE NUMBERS

2 casing
10 window to process space
15 window

17 window frame
20 cavity
30 sealing means
40 light guide
50 lens
55 mirror
60 window frame
61 connection
62 connection
80 pipeline
85 screw connection Thus, a pressure probe and a method of monitoring a process space are disclosed. While embodiments of the invention have been shown and described, it will be apparent to those skilled in the art that many more modifications are possible without departing from the inventive concepts herein. The invention, therefore, is not to be restricted except in the spirit of the following claims.

What is claimed is:

1. A probe for monitoring a pressurised process space in which one or more hazardous substances occur, the probe comprising:

a casing enclosing a first cavity and having a first window, configured to be brought into contact with the pressurised process space, the first window having a first pressure-tight seal formed between the first cavity and the pressurised process space, and a second window having a second pressure-tight seal formed between the first cavity and a second cavity which is sealed off from the pressurized process space, preventing passage of the one or more hazardous substances to the second cavity, wherein the first pressure-tight seal and the second pressure-tight seal are positioned in the casing to form the cavity;

a first coupling line disposed within the cavity between the first and second windows and configured to guide electromagnetic radiation entering through one of the two windows to the other of the two windows;

a first lens disposed between the first coupling line and the first window;

a second lens disposed between the first coupling line and the second window;

a second coupling line positioned in the secondary cavity and disposed on an opposite side of the second window from the first coupling line, the second coupling line configured to guide electromagnetic radiation to or from the first coupling line; and a third lens positioned in the secondary cavity and disposed between the second coupling line and the second window, wherein the second and third lenses optically couple electromagnetic radiation between the first and second coupling lines through the second window.

2. The probe according to claim 1, wherein the first window is replaceable.

3. The probe according to claim 1, wherein the second window is fixed and integrated pressure-tightly in the casing.

4. The probe according to claim 1, wherein the casing includes connections for flushing the cavity.

5. The probe according to claim 1, further comprising one of a pressure sensor for monitoring the pressure in the cavity and a flushing gas supply and a sensor for recording a substance entering the cavity.

6. The probe according to claim 1, wherein the coupling line is configured as a waveguide.

7. The probe according to claim 1, wherein the coupling line is configured as a light guide.

8. The probe according to claim 7, wherein the probe is configured as a process window.

9. The probe according to claim 7, wherein the probe is configured as an immersible probe.

10. A method for monitoring a process space in which one or more hazardous substances occur, the method comprising:

inputting electromagnetic radiation into a first cavity within a casing, the electromagnetic radiation emerging from a first coupling line outside the first cavity, the first cavity being pressure-tightly sealed-off from the process space, preventing passage of the one or more hazardous substances into the first cavity from the process space with a pressure-tight seal formed between the first cavity and the process space, passing through a first lens outside the first cavity, through a first pressure-tight window, through a second lens disposed within the first cavity, and into a second coupling line disposed within the first cavity; and transmitting, using the second coupling line, the electromagnetic radiation through a third lens disposed within the first cavity, out of the first cavity and into the process space through a second pressure-tight window.

11. The method according to claim 10, further comprising:

receiving the electromagnetic radiation into the first cavity from the process space through a third pressure-tight window lying opposite the second pressure-tight window, through a fourth lens, and into a third coupling line disposed within the first cavity; and transmitting, using the third coupling line, the received electromagnetic radiation through a fifth lens and then through the first pressure-tight window and to a spectrometer.

12. The method according to claim 11, further comprising monitoring the first cavity for indications of substances passing from the process space into the first cavity.

13. The method according to claim 10, further comprising:

receiving the electromagnetic radiation into a second cavity from the process space through a third pressure-tight window lying opposite the second pressure-tight window, through a fourth lens, and into a third coupling line disposed within the second cavity; and transmitting, using the second coupling line, the received electromagnetic radiation through a fifth lens and then through a third pressure-tight window and to a spectrometer.

14. The method according to claim 13, further comprising monitoring at least one of the first cavity and the second cavity for indications of substances passing from the process space into the first cavity or the second cavity, respectively.

15. The method according to claim 10, wherein phosgene occurs as a hazardous substance within the process space.

16. A probe for monitoring a process within a pressurised process space, the probe comprising:

a casing enclosing a cavity and having a first window that is replaceable, configured to be brought into contact with the process space, and a second window is fixed and integrated pressure-tightly in the casing, both windows having a pressure tight seal with the casing to form the cavity;

a first coupling line disposed within the cavity between the first and second windows and configured to guide electromagnetic radiation entering through one of the two windows to the other of the two windows;

a first lens disposed between the first coupling line and the first window;

a second lens disposed between the first coupling line and the second window;

a second coupling line disposed on an opposite side of the second window from the first coupling line, the second coupling line configured to guide electromagnetic radiation to or from the first coupling line; and a third lens disposed between the second coupling line and the second window, wherein the second and third lenses optically couple electromagnetic radiation between the first and second coupling lines through the second window.

* * * * *